(12) United States Patent
Yao et al.

(10) Patent No.: US 10,133,045 B2
(45) Date of Patent: Nov. 20, 2018

(54) OPTICAL POLARIZATION TRACTOGRAPHY METHODS

(71) Applicants: Gang Yao, Columbia, MO (US);
Dongsheng Duan, Columbia, MO (US);
Yuanbo Wang, Columbia, MO (US)

(72) Inventors: Gang Yao, Columbia, MO (US);
Dongsheng Duan, Columbia, MO (US);
Yuanbo Wang, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/223,624

(22) Filed: Jul. 29, 2016

(65) Prior Publication Data

US 2017/0031143 A1  Feb. 2, 2017

Related U.S. Application Data

(60) Provisional application No. 62/198,562, filed on Jul. 29, 2015.

(51) Int. Cl.
*A61B 5/00* (2006.01)
*G02B 21/00* (2006.01)
*A61B 1/00* (2006.01)
*G01N 21/21* (2006.01)

(52) U.S. Cl.
CPC ...... *G02B 21/0028* (2013.01); *A61B 1/00009* (2013.01); *A61B 5/0066* (2013.01); *A61B 5/4519* (2013.01); *G02B 21/008* (2013.01); *G02B 21/0012* (2013.01); *G02B 21/0068* (2013.01); *A61B 5/0059* (2013.01); *G01N 21/21* (2013.01)

(58) Field of Classification Search
CPC . A61B 1/00009; A61B 5/0059; A61B 5/0066; A61B 5/4519; G01N 21/21; G02B 21/0012; G02B 21/0028; G02B 21/0068; G02B 21/008
See application file for complete search history.

(56) References Cited

PUBLICATIONS

Fan et al , Imaging myocardial fiber orientation using polarization sensitive optical coherence tomography, Biomedical Optics Express, Mar. 2013, vol. 4, No. 3, pp. 460-465.*
Wang et al, Optical tractography of the mouse heart using polarization-sensitive optical coherence tomography, Biomedical Optics Express, Nov. 2013, vol. 4, No. 11, pp. 2540-2545.*

* cited by examiner

*Primary Examiner* — Ruth S Smith
(74) *Attorney, Agent, or Firm* — Sandberg Phoenix & von Gontard P.C.

(57) ABSTRACT

High-resolution 3D optical polarization tractography (OPT) images of the internal fiber structure of a target tissue. Manipulation of dual-angle imaging data of the fiber orientation inside a target tissue leads to the determination of 3D imaging properties of the target tissue, allowing transmission of the 3D image properties of the target tissue to an OPT processor to produce high-resolution 3D images.

8 Claims, 12 Drawing Sheets

OPTICAL POLARIZATION TRACTOGRAPHY METHODS

CROSS-REFERENCE TO RELATED APPLICATIONS

This application claims the benefit of U.S. Provisional Patent Application Ser. No. 62/198,562, filed Jul. 29, 2015, which is hereby incorporated herein by reference.

STATEMENT REGARDING FEDERALLY SPONSORED RESEARCH OR DEVELOPMENT

Not applicable.

BACKGROUND OF THE INVENTION

The subject matter described herein relates generally to methods and systems for imaging fiber structure in tissue using optical polarization tractography.

Organized fibrous structures exist in many parts of the body. Examples include the skeletal muscle, heart, cartilage, neural tissues, and dental tissues. Normal fibrous structure in these tissues, in particular, its directional/orientation organization, is essential for maintaining physiological function. As an example, the unique helical-orientation architecture in myocardia fibers is essential for the pumping of blood. Moreover, in all such tissues, the fibrous structure changes under diseased and pathological conditions. A clear understanding of changes in fiber organization will help to better understand disease mechanisms and develop more effective therapy.

In order to assess the structure and function of these fibrous tissues, traditional histological sectioning, with its ability to achieve cellular level resolution, has long been the gold standard. However, histological sectioning is destructive, time consuming, labor intensive, and only practical for sampling a few small areas in fixed tissues. Further, histology processing works inherently in a two dimensional (2D) plane. Therefore it captures only the 2D projection of a three-dimensional (3D) object, which varies with the specific projection angle.

Diffusion-tensor based magnetic resonance imaging (DTI) has recently been established for imaging the global 3D fiber orientation, especially in the brain and heart. However, DTI suffers from a spatial resolution largely limited to the submillimeter range, which is insufficient for thin and small tissues such as blood vessel, cartilage, and small animal (such as the rodent models of human diseases) tissues.

Optical coherence tomography (OCT) has also been utilized on a commercial basis, but still has limits on its ability to provide cellular-level, 3D optical images of fiber orientation free of significant distortion at cellular levels. In order to resolve fibers using OCT images, the OCT resolution should be sufficiently high to detect intensity changes around the fibers or fiber bundles. Image processing methods were commonly applied within an evaluation window to determine the primary orientation inside the window. The size of the evaluation window sometimes reached a few hundreds of micrometers. Therefore, the actual spatial resolution can be greatly compromised in computing the fiber orientation by OCT. In addition, the intensity based image processing may be affected by intensity changes unrelated to fiber organization. For example, OCT intensity images may contain "banding" artifacts in birefringent tissues caused by the residual polarization effects in the imaging system. Such non-fiber related structural changes may cause incorrect fiber calculations. This issue becomes more problematic at greater depths where intensity contrast deteriorates substantially.

What is needed, therefore, is a system and method for providing true 3D images of fiber orientation and structure inside a tissue at the microstructural cellular-level of imaging resolution without significant distortion. Such a system and method would provide a large imaging area at a high imaging speed, and can do so for fresh and/or in vivo tissues without the need of labeling.

Further, it would be highly beneficial to have an imaging system and method which enables quantitative feedback and high resolution images. Such information will provide researchers and clinicians enhanced assistance in distinguishing distressed, diseased or damaged fibrous tissue of various types from their healthy tissue counterparts.

BRIEF SUMMARY OF THE INVENTION

Accordingly, applicants have developed an advanced system for ex vivo and in vivo tissue imaging using optical polarization tractography (OPT) and methods and apparatus related to such systems which address many of the needs of prior imaging systems and provide yet additional advantages. The enhanced OPT systems, methods and apparatus of the invention, i.e., applicants' OPT regimen, are capable of non-destructively providing a true 3D image of 3D fiber orientation at different locations inside a tissue with unprecedented details at the cellular resolution level. Moreover, the OPT regimen of the invention is capable of imaging a large imaging area at a high imaging speed, and can do so in fresh and/or in vivo tissue without the need for sample processing such as labeling. It reconstructs the tissue's internal 3D fiber orientation in 3D space, and, during the process, it overcomes a distortion effect due to refraction at the tissue surface. Thus, applicants' OPT regimen can produce highly manipulable 3D image data which enables the detailed examination of a target tissue in essentially any location and view.

Applicants' OPT regimen provides a system for targeted and/or automated assessment of microstructural details of fibrous tissue organization, and provides a "fiber disarray index" readout and/or image map which may be used by clinicians and researchers for establishing a clinical diagnosis or treatment protocols. Applicants' OPT regimen enables in vivo and ex vivo imaging, including with OPT surgical and dissection microscopes, revealing the fiber structure beneath the tissue surface and at varying depths. Applicants' OPT regimen may be employed on essentially any type of fibrous tissue, including, but not limited to, skeletal muscle, nerve fiber, dental tissue, cartilage, heart and blood vessels.

Accordingly, in a first aspect, a method of obtaining 3D optical polarization tractography (OPT) images of a target tissue is provided. The method includes making an initial OPT imaging of the fiber orientation of the target tissue sample using an incident light source thereby producing a first image volume, then making at least one additional OPT imaging of the fiber orientation of the target tissue using one or more projection planes different from the initial fiber orientation thereby providing dual-angle imaging data and producing at least a second image volume. The method further includes determination of an intersection line of at least two different projection planes, whereby the 3D image properties of the target tissue become known; and, transmitting the 3D image properties of the target tissue to an OPT processor to produce a 3D image of the fiber orientation in the target tissue.

In particular embodiments, the dual angle measurements can be simultaneously acquired using a specific implementation such as use of two incident lights at differing angles. These two or more incident lights can be from two or more OPT systems. Or the incident light from the single OPT system can be split into two beams which can be incident upon the sample at different angles. Also, this method can include the registration of the tissue volumes imaged at different angles as described below and detailed herein.

To ensure or enhance the accuracy of 3D orientation measurements, the invention provides a method for registering at least two 3D OPT image volumes. The method includes identifying one or more image features of the tissue volume. The method further includes rotating and/or translating at least one of the at least two 3D OPT image volumes and comparing the 3D locations of the image features identified. Based on the comparison using a pre-selected optimization procedure, a combination of rotation and translation of the OPT image volumes is determined that reduces or minimizes the differences of the 3D locations of the image features between the at least two 3D image volumes.

Additionally, a method for enhancing correctly locating the measurement plane in each OPT is provided. This method corrects surface refraction distortion effects in the OPT scanning of a tissue sample. The method includes the steps of identifying a tissue sample having a surface boundary and identifying the surface boundary. The surface normal vector and the light direction inside the sample after refraction are calculated. The tissue sample's actual pixel coordinates are calculated. These steps can be repeated for any desired location on the entire tissue surface. A new image matrix minimizing the refraction distortions is then constructed for image projection using a 3D, e.g., bi-cubic, interpolation based on the tissue sample's actual, or at least, more accurate, pixel coordinates.

In yet a further aspect, a method for predicting candidates of tissue distress using a "fiber disarray index" (FDI) is also provided. The method includes the steps of obtaining OPT images or data of a target tissue, applying an FDI calculation to the OPT images or data of the target tissue, and thereby determining portions of the target tissue which are predicted to be candidates of tissue distress.

Another aspect of the invention relates to an OPT surgical or dissecting microscope. The OPT microscope includes an illumination system including an illumination source, a microscope configured for use in a surgical or dissection operating setting, and an OPT system retrofitted to work in conjunction with the microscope to provide an OPT imaging capability.

In a final aspect, a system for in situ imaging of a target tissue is provided. The system includes an OPT imaging system, a device for scanning a target tissue in situ, a system for transmitting data obtained from the scanning of the target tissue required for OPT image construction to an OPT image processor.

BRIEF DESCRIPTION OF THE FIGURES

The presently disclosed subject matter will be better understood from reading the following description of non-limiting embodiments, with reference to the attached drawings, wherein below.

DETAILED DESCRIPTION OF THE INVENTION

The foregoing summary, as well as the following detailed description of certain embodiments will be better understood when read in conjunction with the appended figures. As used herein, an element or step recited in the singular and proceeded with the word "a" or "an" should be understood as not excluding the plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments as described and shown herein provide an enhanced system for optical polarization tractography (OPT) imaging as developed by applicants. Applicants' enhanced OPT system using dual-angle imaging enables true three-dimensional (3D) images of the fiber structure inside the tissue with cellular level resolution. Moreover, applicants have devised such a system and method which allows for optimum registration of the 3D imaging and to remove surface refraction effects which distort the orientation of the OPT measurement plane. Further, applicants' OPT system and method includes means for providing the "fiber disarray index" readouts and fiber tissue image mapping that are useful both for clinical diagnosis and for therapeutic treatment protocols. Additionally, the OPT regimen and system are devised to be capable of providing ex vivo and in vivo images of fresh or living tissue, without labeling, including OPT surgical and dissection microscopes.

Applicants' OPT system utilizes "polarization" information, i.e., information provided by such properties as birefringence, diattenuation, and optic axis properties, created by reflected light in order to ascertain additional imaging information for fibrous tissue. Using this stream of information, applicants construct true 3D ex vivo and in vivo tissue images, preferably non-destructively, having a resolution at the cellular level and providing the other benefits described herein.

According to the invention, a local optic axis and other polarization-related data for a target tissue is obtained using a Jones-matrix polarization-sensitive optical coherence tomography (PSOCT) system and method. The core of the hardware for the OPT regimen of the invention is the Jones matrix PSOCT system (JMOCT), an advanced version of PSOCT.

Figure 1:
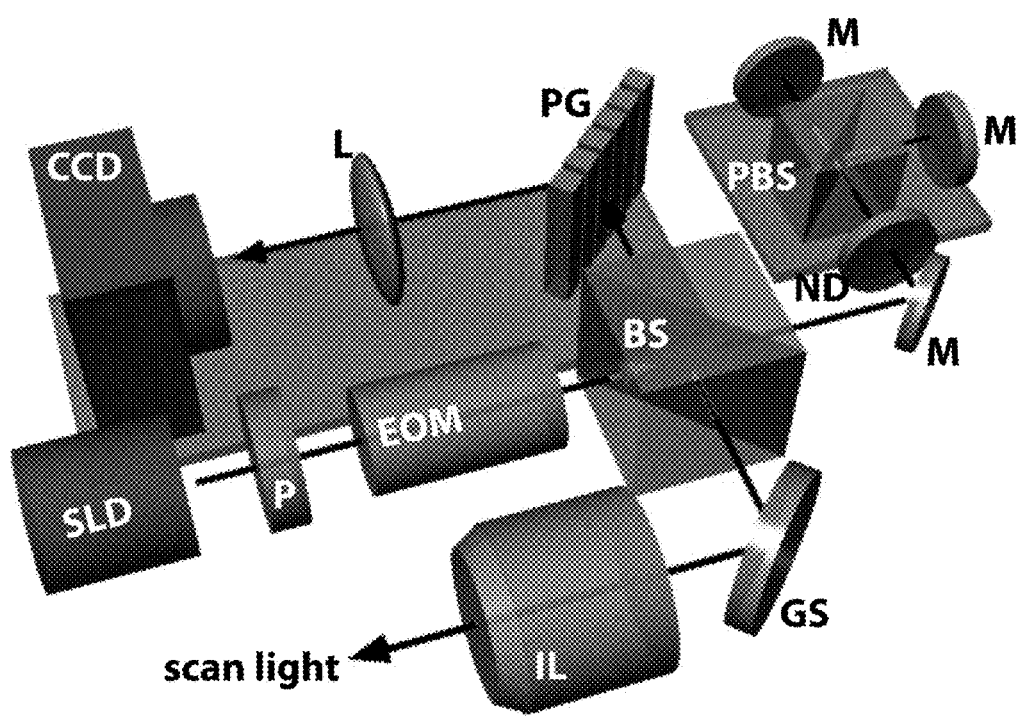
FIG. 1 is a schematic depiction of the OPT system in accordance with an exemplary embodiment of the present invention, wherein BS: beam-splitter. CCD: charge coupler device. EOM: electro-optical modulator. GS: galvanometer scanner. IL: image lens. L: lens. M: mirror. ND: neutral density filter. P: polarizer. PBS: polarized beam-splitter. PG: phase grating. SLD: superluminescent diode.

A schematic depiction showing an embodiment of the OPT apparatus components of a system of the invention is set forth in FIG. 1. In this embodiment, a bulk-optic superluminescence diode source at a central wavelength of 0.85 micrometers is employed, resulting in a 3.9 micrometer axial resolution and 12.4 micrometer lateral resolution. Described generally, as depicted in the representative exemplary embodiment shown in FIG. 1, the OPT imaging apparatus includes a radiation, e.g., a light source (here, a superluminescent diode, or SLD); an isolator, which directs the light to a first lens, and which leads to the incident polarizer (P) for generating vertically polarized light. This leads in turn to the electro-optical modulator (EOM) to achieve alternating left-circularly and right-circularly polarized light. The modulated light is then split 50:50 by a beam splitter (BS) into a reference arm and a sample arm. Off-axis scanning via a galvanometer scanner (GS) in the sample arm is used to achieve full range measurement. The sample light is focused into the sample using an imaging lens (IL). In the reference arm, two co-axial reference beams are formed with different delays for the horizontally and vertically polarized beams by using mirrors (M) and a polarization beam splitter (PBS). The reference light intensity can be attenuated using a neutral density filter (ND). This setup maps the horizontally and vertically polarized components of the signal to two separate depth positions in the reconstructed image. The interference OCT signal is detected by a detector. In the embodiment depicted in FIG. 1, the detector is a custom spectrometer constructed using a phase grating (PG), a lens (L) and a near-infrared line-scan camera (CCD). The spectral camera, EOM and scanners are synchronized using trigger signals.

In an exemplary application of applicants' OPT system employing this embodiment, the pixel-wise Jones matrices of an 8×8×1.1 mm$^3$ sample volume (2000×1000×280 pixels in B×C×A scans) may be imaged in, e.g., 80 seconds.

The polarization image data is fed to a computer with software employing an iteration algorithm according to applicants' OPT system to drive data-gathering of and from the local polarization properties of the target tissue, including, e.g., its optic axis, birefringence, and diattenuation properties. See Fan and Yao. Biomed. Opt. Express 4:460 (2013). The final 3D dataset may be interpolated in the lateral directions to obtain the same pixel size of, e.g., 3.9μm in all A-, B-, and C-scans.

Figure 2:
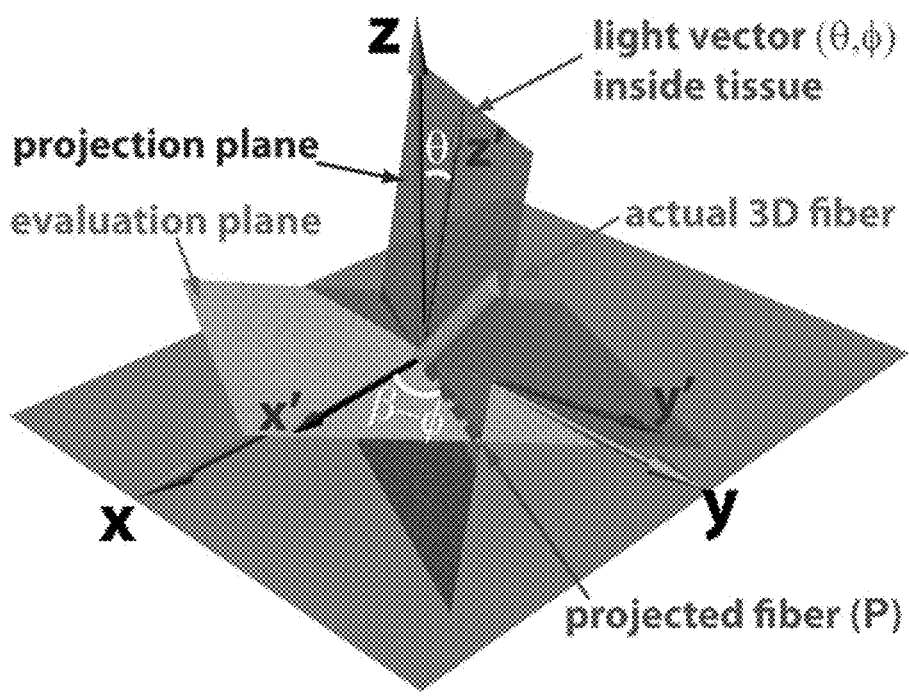
FIG. 2 is an alternative depiction of the imaging geometry of the OPT system of the exemplary embodiment of the present invention shown in FIG. 1.

In a preferred embodiment according to the OPT method of the invention, as depicted in Fig. 2, a fibrous tissue sample is imaged in a laboratory coordinate system formed by the orthogonal x-, y-, and z-axis corresponding to the C-, B-, and A-scan directions. The light is initially incident along the z-axis, but is refracted to the z'-axis inside the sample. The refracted light z' inside the tissue forms a polar angle of θ with the original incident direction (z-axis), which leads to a new x'-y'-z' coordinate. The refracted light (z') can be fully characterized using the polar angle θ and an additional azimuthal angle φ in relation to the x-y-z coordinate. OPT measures the projected fiber (P) orientation β within the evaluation plane (x'-y') which is perpendicular to the light direction (z'). The "actual 3D fiber" lies within the projection plane formed by the light and the 3D fiber.

In this embodiment, the light (the z' axis in FIG. 2) inside the tissue sample after surface refraction may be obtained based on Snell's law using the incident vector $I=[I_x, I_y, I_z]$ and the surface normal vector $N=[N_x, N_y, N_z]$ at the incident point:

$$L=[L_x, L_y, L_z]^T = I/n + (\cos\theta_i - \sqrt{n^2 - \sin^2\theta_i}) N/n, \quad (1)$$

where n is the tissue refractive index. The $\theta_i$ is the incident angle:

$$\cos\theta_i = -N \cdot I. \quad (2)$$

In certain embodiments, the light vector L may also be presented using the following vector based on a polar angle θ and an azimuthal angle φ: $L=[\sin\theta\cos\phi, \sin\theta\sin\phi, \cos\theta]$, where the (θ, φ) is calculated using the vector L=[Lx, Ly, Lz] constructed in Eq. 1:

$$\begin{cases} \theta = \cos^{-1} L_z \\ \phi = \tan^{-1} \dfrac{L_y}{L_x} \end{cases} \quad (3)$$

In general, the orientation β measured in certain embodiments of applicants' OPT system and method represents the projected fiber within the evaluation plane (x'-y' in FIG. 2 and in relation to the x-axis. Thus, the vector representing the projected fiber (as seen in FIG. 2) may be expressed in the laboratory coordinate system (x-y-z) as:

$$P = \begin{bmatrix} \cos\theta\cos\phi\cos\gamma - \sin\phi\sin\gamma \\ \cos\theta\sin\phi\cos\gamma + \cos\phi\sin\gamma \\ -\sin\theta\cos\gamma \end{bmatrix}, \quad (4)$$

where γ=β−φ.

Dual-Angle 3D OPT Images

Applicants' OPT enhanced system and method additionally provide for true 3D images by the use of a dual-angle imaging process. In the dual-angle imaging approach, to achieve true 3D images of the 3D fiber orientation, an initial OPT imaging of the fiber orientation inside a target tissue is carried out, e.g., as described above. The actual 3D fiber is not determined, however, by a single OPT measurement. According to this aspect of the invention, the fiber is located within the projection plane (See FIG. 2) formed by the incident light and the projected fiber, and the fiber orientation is measured at least a second time using a different projection plane.

Upon making such a "dual-angle" measurement, the 3D fiber may be fully determined as the intersection line of the two projection planes. In accordance with an embodiment of the invention, this second measurement may be performed by rotating the sample, or, alternatively, by rotating the incident light in a predefined way. This projection plane corresponding to the light direction (θ, φ) and projected fiber orientation γ=β−φ is thereby identified using its normal vector M calculated as the cross-product of P and L:

$$M = P \times L = \begin{bmatrix} \sin\theta\cos\gamma + \cos\theta\cos\phi\sin\gamma \\ -\cos\phi\cos\gamma + \cos\theta\sin\phi\sin\gamma \\ -\sin\theta\sin\gamma \end{bmatrix}. \quad (5)$$

If the second measurement produces a different light direction (θ', φ') and results in a projected fiber orientation γ'=β'−Φ', the 3D fiber orientation may then be determined as:

$$F = M \times M' = \begin{bmatrix} \sin\theta\cos\gamma + \cos\theta\cos\phi\sin\gamma \\ -\cos\phi\cos\gamma + \cos\theta\sin\phi\sin\gamma \\ -\sin\theta\sin\gamma \end{bmatrix} \times \begin{bmatrix} \sin\phi'\cos\gamma' + \cos\theta'\cos\phi'\sin\gamma' \\ -\cos\phi'\cos\gamma' + \cos\theta'\sin\phi'\sin\gamma' \\ -\sin\theta'\sin\gamma' \end{bmatrix}. \quad (6)$$

In an embodiment of the dual-angle construction of the invention, a registration of the two image volumes measured at γ and γ' (or in some cases multiple image volumes) is carried out. This can be achieved by transforming (rotating and translating) one (or more) 3D image volume to substantially match the target image volume, thereby minimizing the location differences of the image features between the 3D image volumes. Multiple image features can be used to determine the best transformation. For example, any particular structures inside the tissue that appear to be distinct from its surroundings can be used as markers to register the images. In addition, the surface of the tissue image volume can be used for image registration. The sample surface profiles can be quantified using the distance between each pixel on the surface and a standard imaging plane (e.g., the plane of the en face plane at z=0). When the two image volumes are registered, i.e., the locations of the identified image feature(s) should coincide, and their surface profiles will overlap with each other. An optimization procedure in computer program can be applied to automatically rotate and translate one image volume and calculate the differences of the locations of all identified features between two or more image volumes. The computerized optimization procedure iterates this process to find the best transformation to register the two or more image volumes. Since the precision of image registration determines the eventual accuracy in 3D fiber calculation, it is quite useful to achieve pixel-level accuracy in image registration.

Surface Refraction Correction

In another aspect of the OPT system and method of the invention, a correction is made for a significant image distortion which applicants discovered is created by surface refraction of imaged depth-resolved target tissue. This corrective procedure provides cellular-level microstructural details essentially equal to those provided by histological analysis.

As discussed, the refraction at the tissue surface changes the light direction inside the tissue. Therefore the evaluation plane (FIG. 2) is also changed at different depths inside the tissue. In addition, a uniform scanning grid of the incident light on the sample surface becomes distorted inside the sample. The amount of distortion generally depends on the specific incident angle and the depth of the evaluation plane. To correct such distorting surface refraction effect, the sample surface boundary is identified. An intensity-based thresholding method may be used. See Wang et al. Biomed. Opt. Express 5:2843 (2014). In a preferred embodiment, a 5×5 pixel median filter, e.g., is applied to remove noisy pixels on the resulting 2D surface. The light direction (θ, φ) inside the sample after refraction may be calculated using Eqs. (1) and (2) above.

According to this embodiment, the actual pixel coordinate [i', j', k'] for the original pixel [i, j, k] may be calculated as:

$$\begin{cases} i' = i + k\sin\theta\cos\varphi \\ j' = j + k\sin\theta\cos\varphi \\ k' = k\cos\theta \end{cases}. \quad (7)$$

A new rectangular 3D image matrix may then be computed using a 3D bi-cubic interpolation based on the above actual pixel coordinates. In this exemplary embodiment, the M vector (Eq. 5) is obtained for each pixel in the 3D dataset.

Fiber Tissue Distress Imaging and Applications

Applicants' OPT regimen includes application of a "fiber disarray index" (FDI), optionally supplemented by a local retardance calculation, to produce the fiber stress pattern readout and/or image map of stressed, damaged and/or diseased fibrous tissue. The regimen may be configured to provide assistance to clinicians and researchers addressing particular pathologies.

Various pathologies, e.g., inflammation, can lead to damaged fibers. The damaged fibers may be identified by fragmentation or by showing "disarrayed" patterns which may be established quantitatively as being different from, and distinguishable to, their comparable normal tissue patterns. Such a quantitative "disarrayed" pattern may be located by performing mathematical image processing algorithms over a targeted portion, or the entire, imaged volume of the tissue, thus identifying areas which show higher variation in fiber orientation distribution, i.e., they mark areas where the fiber is damaged or diseased. Thus, according to this aspect of the invention, an FDI is established by which healthy and "distressed" tissues are distinguished. The results of these FDI calculations can be used to generate data, and data readouts regarding, and FDI image mapping of, distressed or damaged tissue. In turn, these tools may be used by clinicians to assist them in diagnosing damaged or diseased tissue for further investigation, or for targeted treatments. They may also be utilized by researchers and industry to investigate new drug and therapeutic regimens and treatment protocols.

According to this aspect of the invention, a "threshold" of FDI may be established, e.g., using clinical (or other sources of) data contrasting a known damaged/diseased tissue with a normal tissue of a specific type to establish the FDI algorithm (See Exs. 6 and 7, below) which may be used to automatically identify the distressed tissue. This FDI algorithm, based on determination of a calculated threshold, is then applied to the data acquired by the OPT system and method of the invention to prepare the data readouts and/or FDI image maps. See Exs. 6 and 7. Thus, locations where the FDI is higher than the FDI threshold may be labeled such as by using a colored light, or other distinctive illumination of the distressed tissue area, to indicate potential sites of candidates for further pathological assessment. Such assessment may be conducted using a 3D OPT system or in situ imaging, especially using an OPT microscope, as described elsewhere in this application.

In Vivo and Ex Vivo Imaging

Applicants also provide an OPT regimen for in vivo or ex vivo imaging, including use of an OPT microscope for viewing and dissecting fibrous tissue.

According to this aspect of the invention, the OPT system of the invention is adapted for use or retrofitted to be used with and/or coupled to a surgical or dissection microscope to provide for in situ, in vivo or ex vivo visualization of tissue structures during surgery or tissue dissection. See U.S. Pat. Nos. 7,889,423; 8,049,873; and 8,777,412, which are incorporated by reference as though fully set forth herein for additional details on applying applicants' OPT system and method to surgical and dissection microscopes.

Figure 3:
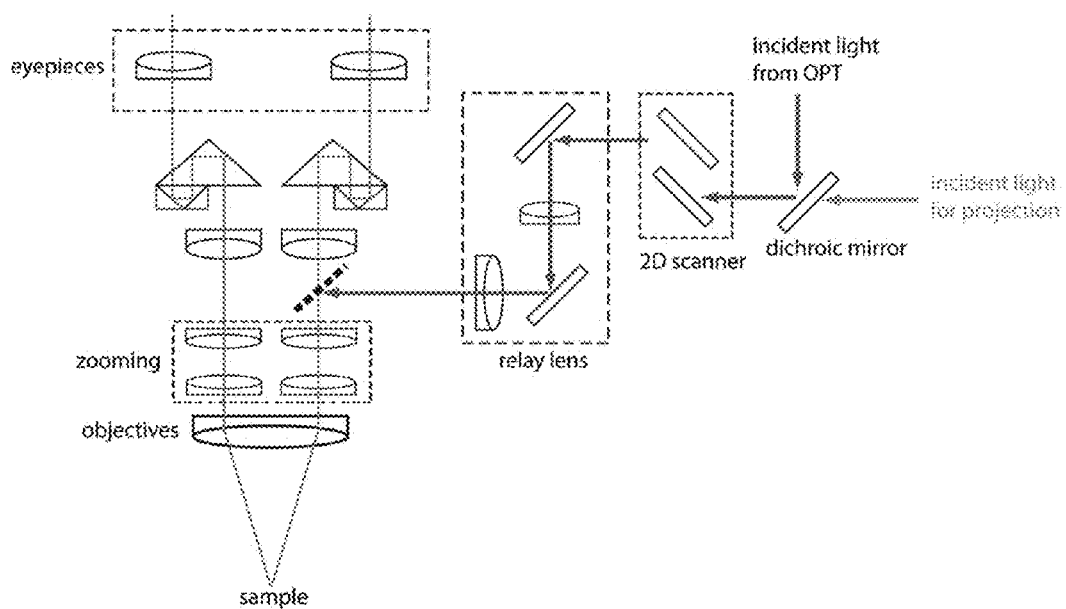
FIG. 3 is a schematic diagram showing an exemplary embodiment of the OPT microscope system for in vivo and ex vivo visualization.

A schematic diagram showing the OPT microscope for in vivo visualization is shown in FIG. 3.

In the aforementioned exemplary embodiment, the "incident light" from the OPT system (FIG. 1) can be steered using a "2D scanner" (FIG. 3). The scanning beam can be coupled into a generic 20× binocular dissecting microscope using a beam splitter. The microscope head (including eyepieces, zooming lens and objectives) can be machined to mount a flange for interface with the OCT system via a standard cage system. The coupled incident light is focused upon the "sample" via the "zooming" lens and the objective of the microscope. A "relay-lens" system (FIG. 3) can be designed to achieve a redefined imaging area with a specific resolution. Another incident light for projection (see next paragraph) can be coupled with the incident light using a "dichroic mirror". As an additional example, the optical beam can be incorporated into optical fibers which can be then used in an endoscope to enable OPT imaging in endoscopic applications.

In general, once tissue damage is detected using markers such as the FDI, the FDI image may be projected back to the tissue sample. In an exemplary embodiment, the projection system is designed to share the same scanning system already used in the OPT system of the invention. In one embodiment, an "incident light for projection" at another wavelength (e.g. green light) is used for the projection component to achieve better visual contrast. Such a projecting light can be integrated with the OPT microscope system using a dichroic mirror (FIG. 3). This projection allows for direct visualization of tissue damage or structure on the sample surface. This may provide guidance for the OPT microscope operator to inspect the tissue in situ or to dissect tissue for further pathological analysis.

In the aforementioned exemplary embodiment, the measured fiber orientation can also be projected back to the tissue surface so that the surgeon and other operators can clearly see it during, e.g., transplantation surgery. This provides a way for the surgeons to rotate the transplant grafts or materials to match their fiber structure with that of the host. Such a capability can improve the transplant outcome in cartilage repair, blood vessel repair, and many other grafting procedures.

EXAMPLES

Dual-Angle 3D Imaging

In Examples 1 and 2, dual-angle measurements were obtained by imaging the tissue sample at two different rotational angles ($\gamma_1$ and $\gamma_2$) around the C-scan direction to obtain two datasets for M at ($\theta$, $\phi$, $\beta$) and M' at ($\theta'$, $\phi'$, $\beta'$), respectively. To register these two new 3D datasets, the 3D image for M' measured at $\gamma_2$ around the C-scan direction was rotated back around the C-scan. All image processing was implemented using Matlab.

Example 1

Demonstration of the 3D OPT System in a Small Piece of the Mouse EDL Muscle

The dual-angle 3D OPT system and method according to an embodiment of the invention was demonstrated by imaging a small piece of the mouse EDL muscle which was placed at known orientations in the space. The middle of the EDL muscle had relatively homogeneous myofiber orientation. The muscle sample was fixed in 10% paraformaldehyde after excising it from the animal.

Figure 4:
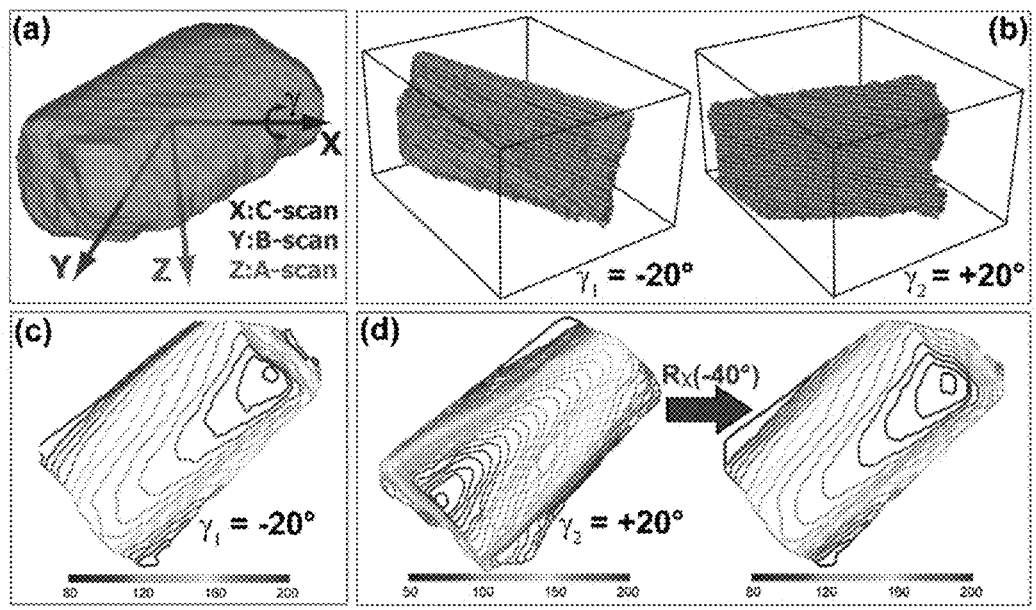
FIG. 4 provides images illustrative of the dual-angle 3D OPT imaging of the invention in the extensor digitorum longus (EDL) muscle and image registration.

FIG. 4(a) illustrates the geometry of the EDL muscle in the dual-angle OPT imaging wherein the EDL sample was rotated in the laboratory coordinates by $\gamma_1$ and $\gamma_2$ around the x-axis to complete the dual angle imaging. The muscle sample was mounted on a two-axis rotation stage carefully aligned with the scanning directions to provide accurate rotation around the x-axis (C-scan) and y-axis (B-scan). To implement the dual-angle scanning, the EDL muscle was first scanned at $\gamma_1=-20°$ respect to the x-axis (C-scan); then imaged again at $\gamma_2=+20°$ after rotating the sample by 40° around the x-axis. FIG. 4(b) shows the conventional single-scan OPT of the EDL muscle at the two angles ($\gamma_1$ and $\gamma_2$, e.g., $-20°$ and $+20°$, respectively) which were later used for dual-angle reconstruction. The fiber orientation measured in the single-scan OPT was the 2D projected angle of the 3D fiber in the evaluation plane (FIG. 2). Such projected tractography was constructed within the equi-transmural layer from the tissue surface.

Before the dual-angle construction, the two image volumes measured at $\gamma_1$ and $\gamma_2$ were registered. Their surface profiles were used as the image features for registration. As expected, the "contour" profiles of the sample surface obtained at $\gamma_1=-20°$ (FIG. 4(c)) and $\gamma_2=+20°$ (FIG. 4(d)) were noticeably different due to their different image positions. To register the sample surface measured at $\gamma_2=+20°$ with that obtained at $\gamma_1=-20°$, the image data acquired at $\gamma_2=20°$ was rotated back by 40° by multiplying $R_x(-40°)$ to the 3D coordinates of each image pixel, where $R_x$ is the standard rotational matrix around the x-axis. The resulting surface (FIG. 4(d)) appeared very similar to the one shown in FIG. 4(b). Due to alignment error of the rotational stages, the optimal rotation angle was optimized within a small range (<2°) to minimize the pixel-wise error between the two surface profiles. Quantitatively, 95% of the sample surface had <5-pixel difference after registration.

Figure 5:
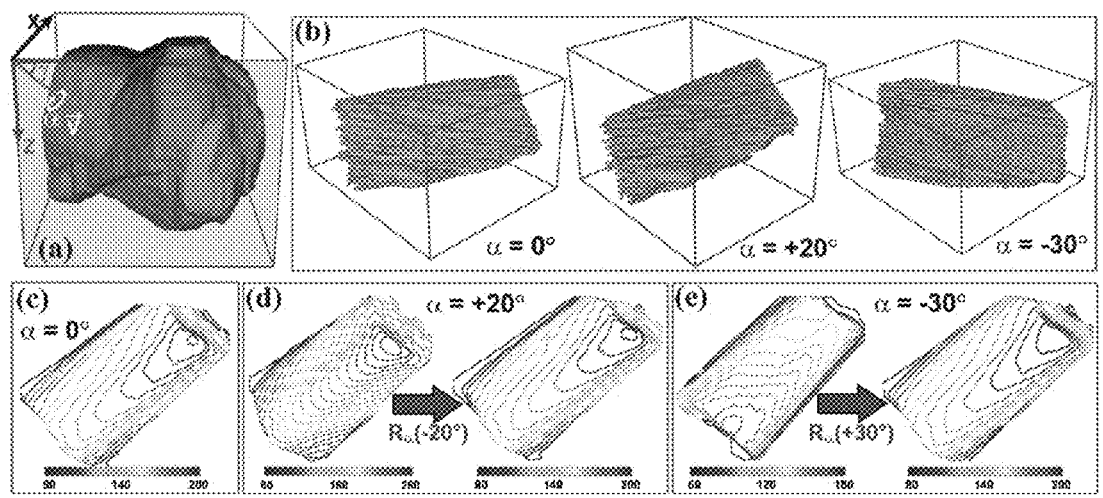
FIG. 5 provides images illustrative of the dual-angle 3D OPT imaging of the EDL muscle placed at various positions in space and the corresponding image registration.

The muscle sample was imaged multiple times when placed at different rotational angles around the y-axis (B-scan) from $\alpha=-30°$ to $+20°$ in a step of 10° around an axis V in the y-z plane (FIG. 5(a)). The rotational axis V had a polar angle of ($90°-\gamma_1$) with the z-axis. Two example 3D image volumes obtained at $\alpha=-30°$ and $+20°$ were illustrated in FIG. 5(a). These six positions induced considerable changes of fiber orientation in the three orthogonal projection planes (x-z, y-z, and x-y for AC, AB, and BC, respectively). The coordinates and axis V shown in FIG. 5(a) were actually located inside the tissue during the experiment (see FIG. 4(a)).

At each sample position $\alpha$, the 3D fiber orientation was calculated using the dual-angle OPT obtained at $\gamma_1=-20°$ and $\gamma_2=+20°$. FIG. 5(b) shows example 3D tractography when the EDL muscle was placed at α=0°, +20°, and −30°. Instead of the 3D images of 2D projected angle shown in FIG. 4(b), the tractography in FIG. 5(b) represented the 3D fiber orientation in 3D space. These images constructed at different positions (a) were also registered to each other using the same procedure applied in registering the dual-angle images.

FIGS. 5(c), 5(d), and 5(e) show the tissue surface imaged at α=0°, α=+20°, and −30° respectively, and after rotating back by +30° and −20° around the validation axis V. All these surface contours were associated with the first position of the dual-angle imaging at $\gamma_1$=−20°. These surface contour patterns showed significant difference because the EDL muscle was imaged from different angles. However, after rotating the image volume back around the axis V (FIG. 5(a)), the resulting surface contours in FIGS. 5(d) & 5(e) appeared quite similar to the sample surface imaged at α=0°. In all cases, 92% of the surface area had <5-pixel difference after rotation, which confirmed the goodness of the image registration.

For the purpose of validation, the directly measured 3D fiber angle at a sample position a was compared with the "expected" angles calculated using 3D fiber angle measured at α=0°. The "expected" 3D fiber direction $F^e(\alpha)=[f_x(\alpha), f_y(\alpha), f_z(\alpha)]^T$ at sample position α can be calculated from the 3D fiber direction F(0) measured at sample position α=0:

$$F^e(\alpha)=R_v(\alpha)F(0)=[R_x(-\gamma)R_y(\alpha)R_x(\gamma)]F(0), \quad (8)$$

where $R_x$ and $R_y$ are standard rotational matrices around the x- and y-axis, respectively. To facilitate the comparison among 3D angles, we compared the 2D projected angles of the 3D direction in the three orthogonal projection planes:

$$\begin{cases} \theta_{AC} = \tan^{-1}(f_z/f_x) = \tan^{-1}(\cot\theta_f/\cos\phi_f) \\ \theta_{AB} = \tan^{-1}(f_z/f_y) = \tan^{-1}(\cot\theta_f/\sin\phi_f) \\ \theta_{BC} = \tan^{-1}(f_y/f_x) = \phi_f \end{cases} \quad (9)$$

Figure 6:
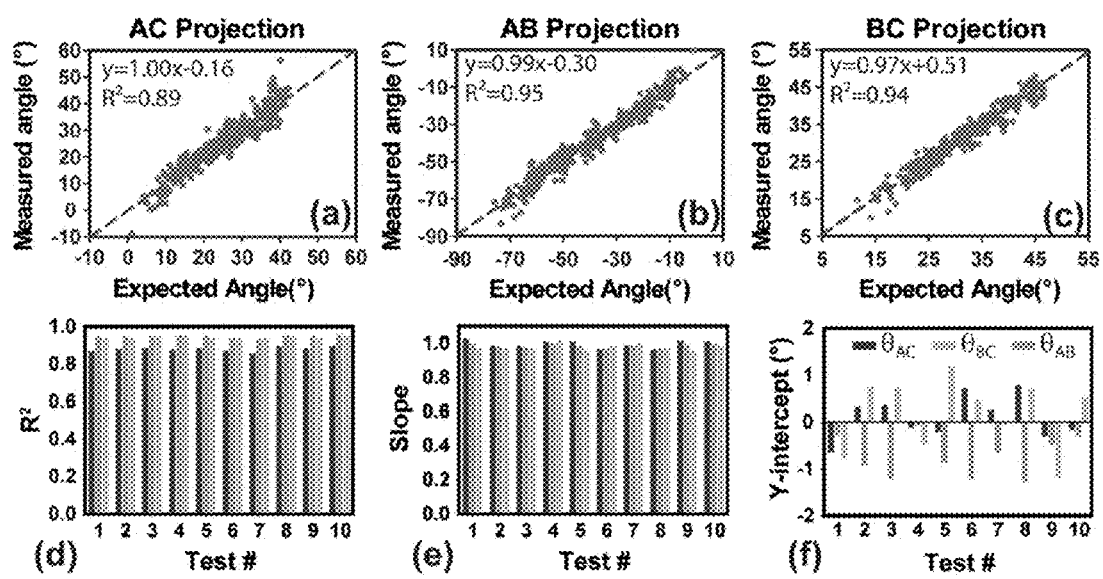
FIG. 6 provides images illustrative of the dual-angle 3D OPT imaging of the EDL muscle in comparison with theoretical prediction.

FIG. 6 shows the validation results obtained from 50 randomly selected ROIs (size 48×48×48 μm³) in a 0.3×0.3×1.0 mm³ (A×B×C) volume of the EDL muscle. Since each ROI was measured in six different sample positions from α=−30° to +20°, there are 300 data points in the correlation analysis of the measured and "expected" projection angles in the AB, AC and BC planes. In all the three projection planes, the "expected" angles were highly correlated with the actual measured angles (FIG. 6). All three linear regression results showed a close to 1.0 slope and ≤0.51° y-intercept. The coefficients of determination ($R^2$) were 0.89, 0.95, and 0.94 in the AB, AC, and BC planes, respectively. These results suggested that the experimentally measured 3D fiber orientation in dual-angle OPT closely followed the "expected" results. Among all data points, the mean and standard deviation of the difference between measured and expected fiber angle were 0.00°±3.30°, 0.00°±4.02°, and 0.14°±1.96° in the AB, AC, and BC planes, respectively.

Similar results were obtained when different sets of ROIs were used in the validation. We repeated ten times the aforementioned procedure of selecting 50 ROIs randomly in the EDL muscle. The mean and standard deviation of the coefficients of determination ($R^2$) were 0.88±0.01, 0.95±0.01, and 0.94±0.01 in the AC, AB, and BC planes (FIG. 6(d)). The corresponding slopes of the linear regression were 0.99±0.02, 0.98±0.01, and 0.98±0.02 (FIG. 6(e)); and the y-intercept values were 0.10±0.46, −0.72±0.44, and 0.19±0.77 (FIG. 6(f)) in the AC, AB, and BC planes respectively.

The above consistent results indicated a high correlation between the dual-angle OPT measurement and the expected values and thus validated the dual-angle OPT in imaging 3D fiber orientation.

Example 2

Imaging 3D Fiber Orientation in the Mouse TA Muscle

Figure 7:
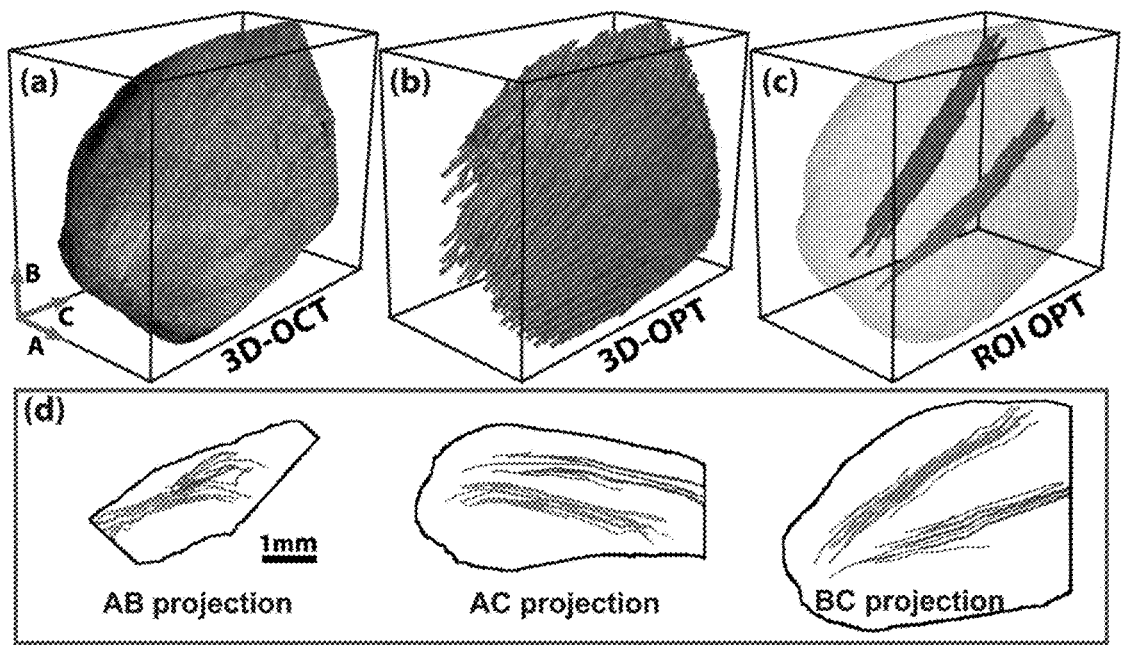
FIG. 7 provides images illustrative of dual-angle OPT of 3D fiber orientation in the mouse tibialis anterior (TA) muscle.

In order to further evaluate the accuracy of the 3D measurements according to an embodiment of the OPT system of the invention, a piece of fixed mouse TA muscle was imaged. FIG. 7(a) shows the 3D intensity images of the TA muscle imaged at $\gamma_2$=+25°, where fibers are difficult to observe. In sharp contrast, the corresponding 3D tractography (FIG. 7(b)) constructed in dual-angle OPT clearly revealed 3D fiber structure. The 3D tractography indicated that the muscle fibers were mostly aligned along the long axis of the TA muscle.

FIG. 7(c) demonstrates the capability of 3D OPT in revealing detailed fiber architecture by selectively revealing two fiber bundles at two separate locations inside the muscle. As expected, the two muscle bundles were clearly organized along the long axis of the muscle toward the apex. FIG. 7(d) further demonstrated that the details of the fiber bundles can be studied in detail by projecting the 3D fiber bundles to the 2D projection planes (the AB, AC, and BC planes).

Example 3

Imaging 3D Fiber Orientation in Cartilage

In this example, dual-angle OPT was applied to image the collagen fiber organization in a piece of bovine articular cartilage. The cartilage sample was excised from the middle phalanx and fixed in 4% paraformaldehyde. This sample was imaged from the cartilage surface (referred to as the "top-scan") using the dual-angle procedures at $\gamma_1$=−25° first and then at $\gamma_2$=+25°.

Figure 8:
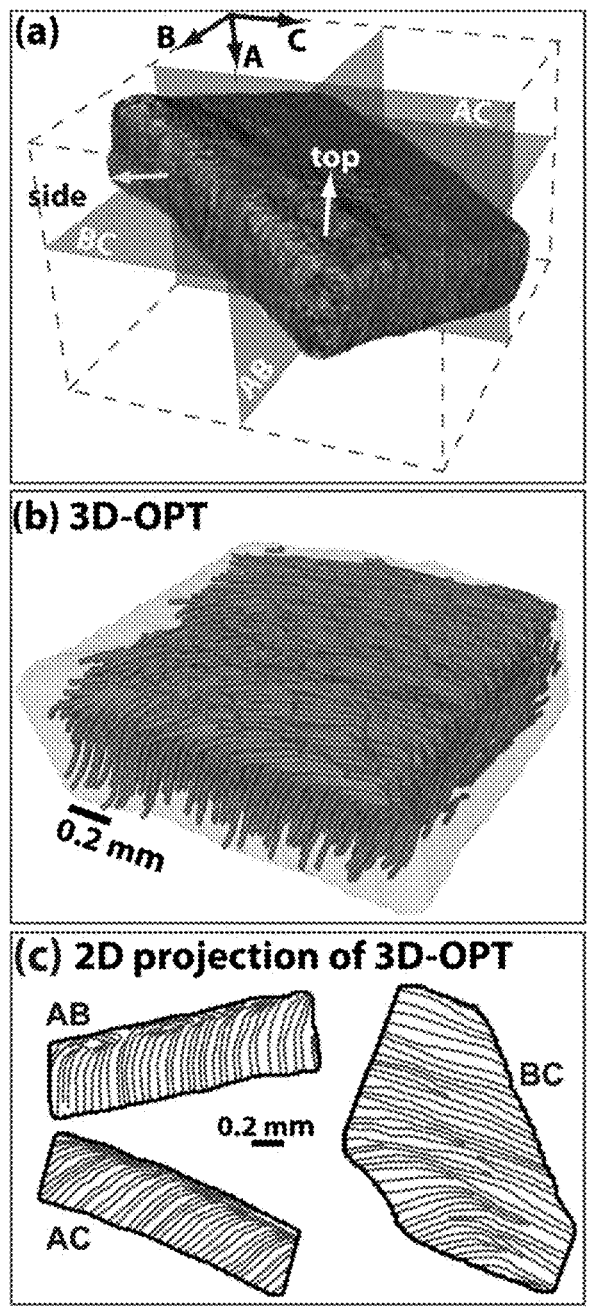
FIG. 8 provides images illustrative of the overall tractographic visualization of a piece of cartilage.

No fibers can be observed from the 3D intensity image of the cartilage sample (FIG. 8(a)). However, the constructed 3D fiber tractography from dual-angle OPT (FIG. 8(b)) clearly revealed the unique arcade-like fiber organization in the cartilage. In the "superficial" zone, fibers were oriented relatively parallel to the sample surface. Then the fibers arched in the "transitional" zone to be eventually perpendicular toward the boundary between non-calcified and calcified cartilage in the deeper "radial" zones. Moreover, the 3D tractography correctly revealed the "brushing" direction, i.e. all fibers were bended toward the same direction.

The 3D OPT data set can be explored programmatically to provide a detailed view of the fiber architecture. Due to the unique "arcade" 3D fiber structure in cartilage, the fiber orientation would appear differently when viewed from different angles or in cutting planes made at different orientations. FIG. 8(c) demonstrated such an effect by showing the fiber organization when projecting the 3D orientation to three orthogonal 2D cutting planes (e.g., AB, AC, and BC planes as labeled in FIG. 8(a)). This result underscored the importance of considering the cutting directions when evaluating the histology and SEM images of cartilage samples

Example 4

Distortion Correction and Comparison to Histology

This example provides an illustration of the removal of surface refraction distortion in an aspect of the OPT system and method of the invention and provides a comparison to histologic processing.

A small piece of the heart tissue of roughly 2~4 mm in size was cut from either the left or right ventricles from a mouse heart. This piece of heart tissue was imaged first using an embodiment of the OPT system of the invention of the type depicted in FIG. 1. Then the tissue sample was embedded in an optimal cutting compound and frozen in liquid nitrogen. For histology processing, the tissue block was cut into 10 μm slices starting from the epicardium side. The histology slices were equivalent to the OCT en face imaging plane, i.e. the plane formed by the B- and C-scan directions at a specific depth from the epicardium. All tissue slices were numbered including damaged slices which, however, were not used in the histology imaging. Tissue sections were stained with hematoxylin and eosin for microscopic imaging using a Nikon Eclipse E800 microscope equipped with a QImaging RETIGA 1300 camera.

Our OPT method was implemented in a spectral domain full-range JMOCT system as described in Fan and Yao. Opt. Express 20:22360(2012). Fiber orientation and tractography were obtained using OPT as described in Wang et al. Biomed. Opt. Express 5:2843 (2014). Due to the labor intensive nature of histology analysis, an intensity-gradient based method was applied to calculate cardiac myofiber orientation in histology images to facilitate the comparison between OPT and histology images (see description in Wang et al. 2014). The OPT and histology images were registered and compared as described in Wang et al. 2014.

To correct surface refraction, the sample surface in the OCT intensity image was first determined using an intensity threshold-based segmentation algorithm (as set out in Wang et al. 2014, incorporated herein by reference as though fully set forth herein). The resulting surface data were represented as a 2D array containing the axial depth position for each pixel on the sample surface. A 5×5 median filter was applied to remove noisy pixels from the data set. The surface normal vector N=[Nx,Ny,Nz] was then calculated by using the "surfnorm" function in MATLAB, a commercially available computer software application.

Figure 9:
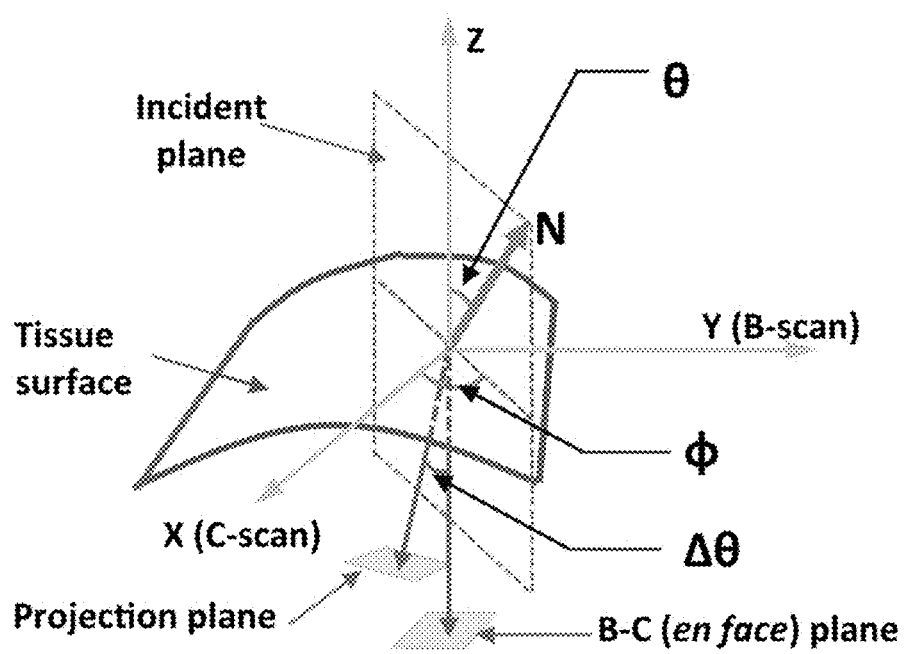
FIG. 9 is a schematic depiction of the image distortion induced by surface refraction.

FIG. 9 provides an exemplary illustration of image distortion induced by surface refraction. The incident light (A-scan) is aligned with the z-axis. (N) indicates the surface normal vector at the light incidence point. As shown in FIG. 9, the surface normal vector N=[Nx,Ny,Nz] can be described using a pair of angles $(\theta, \phi)$:

$$\theta = \tan^{-1}\frac{\sqrt{N_x^2 + N_y^2}}{N_z} \quad (11)$$

$$\phi = \tan^{-1}\frac{N_y}{N_x}$$

X-Y-Z represents the laboratory coordinates. The original incident light is perpendicular to the en face plane formed by the B-C scanning. The en face plane is equivalent to the histology sectioning plane. Due to surface refraction, the incident beam is deviated by an angle of $\Delta\theta$ within the incident plane which is formed by the incident light and the surface normal vector (N) of the tissue surface. Applying geometrical transformation, the actual pixel position (x', y', z') corresponding to the raw pixel (x, y, z) can be calculated as:

$$x'=x+z \sin \Delta\theta \cos \phi$$

$$y'=y+z \sin \Delta\theta \sin \phi,$$

$$z'=z \cos \Delta\theta \quad (12)$$

where the surface refraction induced direction change $\Delta\theta$ can be determined according to Snell's law at the tissue surface:

$$\Delta\theta = \theta - \sin^{-1}\left(\frac{\sin\theta}{n}\right) \quad (13)$$

Figure 10:
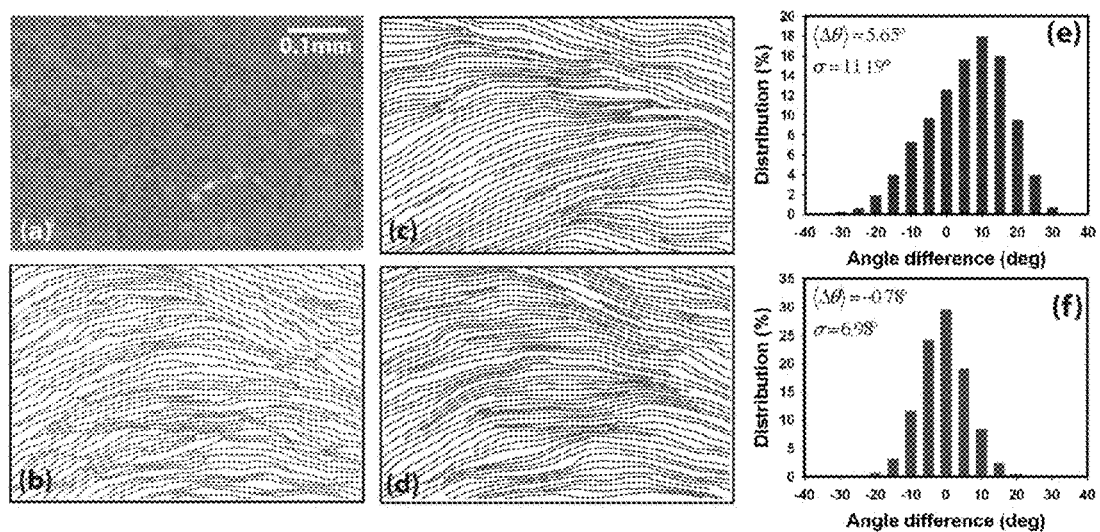
FIG. 10 provides images of an example of surface refraction correction including related histology and OPT images and pixel distributions.

The image distortion due to surface refraction can significantly impact the OPT accuracy. To illustrate this effect, FIG. 10(a) shows an example histology image obtained at a depth of 0.35 mm beneath the epicardium. FIG. 10b) shows the fiber orientation image obtained from the histology image as described above. FIG. 10(c) and FIG. 10(d) show the OPT results before and after correcting the surface refraction.

Without correcting the surface refraction, the OPT results (FIG. 10(c)) were significantly different from the histology tractography (FIG. 10(b)). For example, the central part of the OPT shows positive orientations; whereas the orientation revealed in histology is close to zero degree. In addition, the fibers in the upper left corner of the histology result (FIG. 10(b)) show positive angles; whereas they remain almost horizontal in OPT (FIG. 10(c)). After applying the correction as described above, the resulting OPT (FIG. 10(d)) appears very similar to the histology results (FIG. 10(b)).

To further quantify the differences between histology and OPT, the pixel-by-pixel differences between the two images were calculated. The histology images were resized using cubic spline to match the pixel size of 3.9 μm in OPT. As shown in FIG. 10(e) and FIG. 10(f), the mean difference between histology and OPT was reduced from 5.65° before correction to −0.78° after correction. The correction reduced standard deviation from 11.19° to 6.98°. After the distortion correction, about 85.5% of the 14,959 pixels in this image area (FIG. 10(a)) had a≤10° difference in measured orientation between OPT and histology. Even though this pixel-wise comparison did not reach a perfect 100% match, the corrected OPT (FIG. 10(d)) and histology result (FIG. 10(b)) resembled each other remarkably well.

Examples 5 and 6

Imaging Fiber Organization;Disorganization; Muscle Damage,

Examples 5 and 6 are illustrative of aspects of the system and method of the invention wherein normal and distressed fibrous tissue are imaged and mapped, using, e.g., a Fiber Disarray Index (FDI) or similar calculations applying the same differentiating principles which may be applied in a targeted and/or automated manner to identify tissue distress candidates.

Example 5

Imaging Cardiac Myofiber Organization

The heart is a highly organized helical structure composed of well-oriented myofibers. Such organization enables normal electric signal propagation and coordinated mechanical force production for efficient blood pumping. In other words, the axial orientation of myofibers plays an important role in normal heart function. For example, action potential propagates 2 to 10 times faster along the heart muscle fibers than along the transverse direction. Disruption of normal myofiber architecture in the heart contributes to numerous cardiac diseases such as arrhythmia, dilated cardiomyopathy, hypertrophic cardiomyopathy, and infarction.

Duchenne muscular dystrophy (DMD) is the most common and severe muscle disease caused by mutations in the dystrophin gene. It affects approximately one of every 5,000 male infants. The absence of the dystrophin gene leads to body-wide muscle degeneration and necrosis. Most patients eventually die from respiratory and/or cardiac failure. Animal models have been indispensable in our understanding of DMD and developing therapeutic approaches. The mdx4cv mouse is a commonly used DMD animal model where the dystrophin expression is abolished by a nonsense point mutation in exon.

Figure 11:
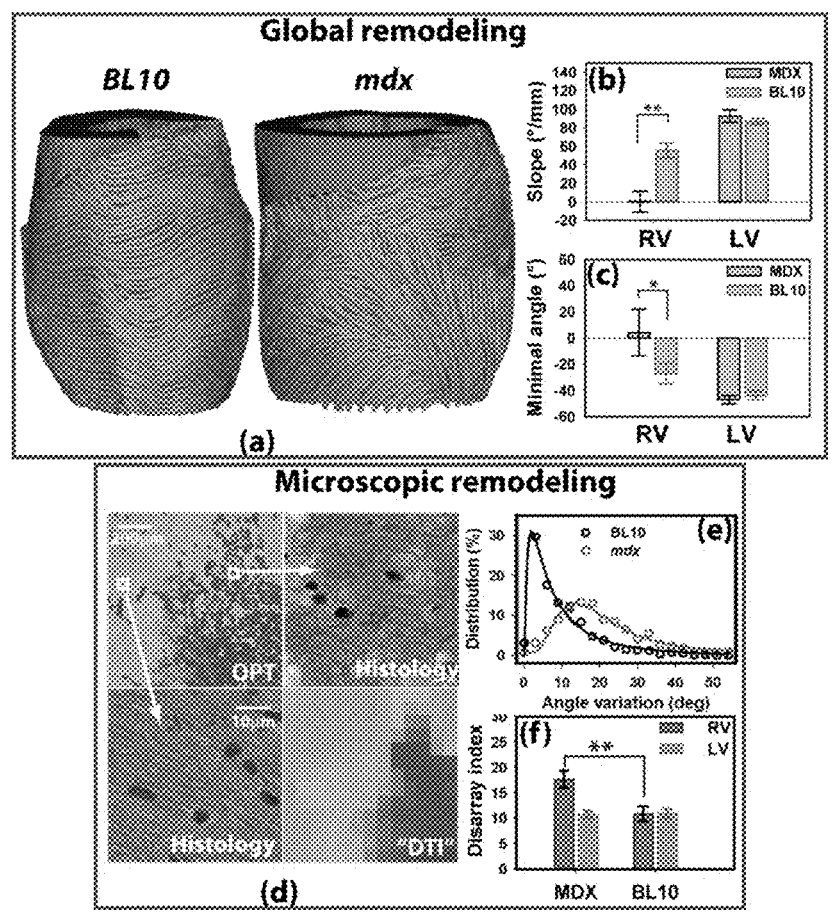
FIG. 11 provides images related to imaging the 3D fiber structure in a fresh whole mouse heart.

The OPT regimen outlined in the schematic in FIG. 1, as set forth above, was used to image freshly dissected intact mouse hearts (See FIG. 11) acquired from normal (BL10) and diseased (mdx4cv) mice. The mdx heart is a model of dilated cardiomyopathy. OPT clearly revealed striking global differences in the right ventricular (RV) wall between the two mice (FIG. 11a). Such reorganization can be quantified using the rate (slope) of the transmural orientation changes across the RV wall (FIG. 11b) and the minimal fiber orientation close to the epicardium (FIG. 11c).

In addition, application of OPT revealed significant cellular-level myofiber disorganization in the RVs of mdx mice (FIG. 11d). Such microscopic fiber disorganization was further confirmed with histology examination (FIG. 11d). Such a micro scale disorganization cannot be observed at a resolution of 100 µm (equivalent to current DTI technology). FIG. 11e shows the distribution of "orientation variation" within a large 3×3 mm² ROI obtained by dividing the ROI into 30×30 sub regions of 100×100 µm² each. A quantitative "fiber disarray index" was calculated by averaging the standard deviation values obtained in each subregion. In the RV wall, the fiber disarray index was significantly higher (p<0.001) in mdx than BL10 (FIG. 11f). No significant difference was observed in LV. Our observation shows an important piece of data to support evidence that DMD cardiomyopathy starts from the right ventricle (RV) likely due to severe diaphragm dystrophy.

Example 6

Imaging Muscle Damage

Figure 12:
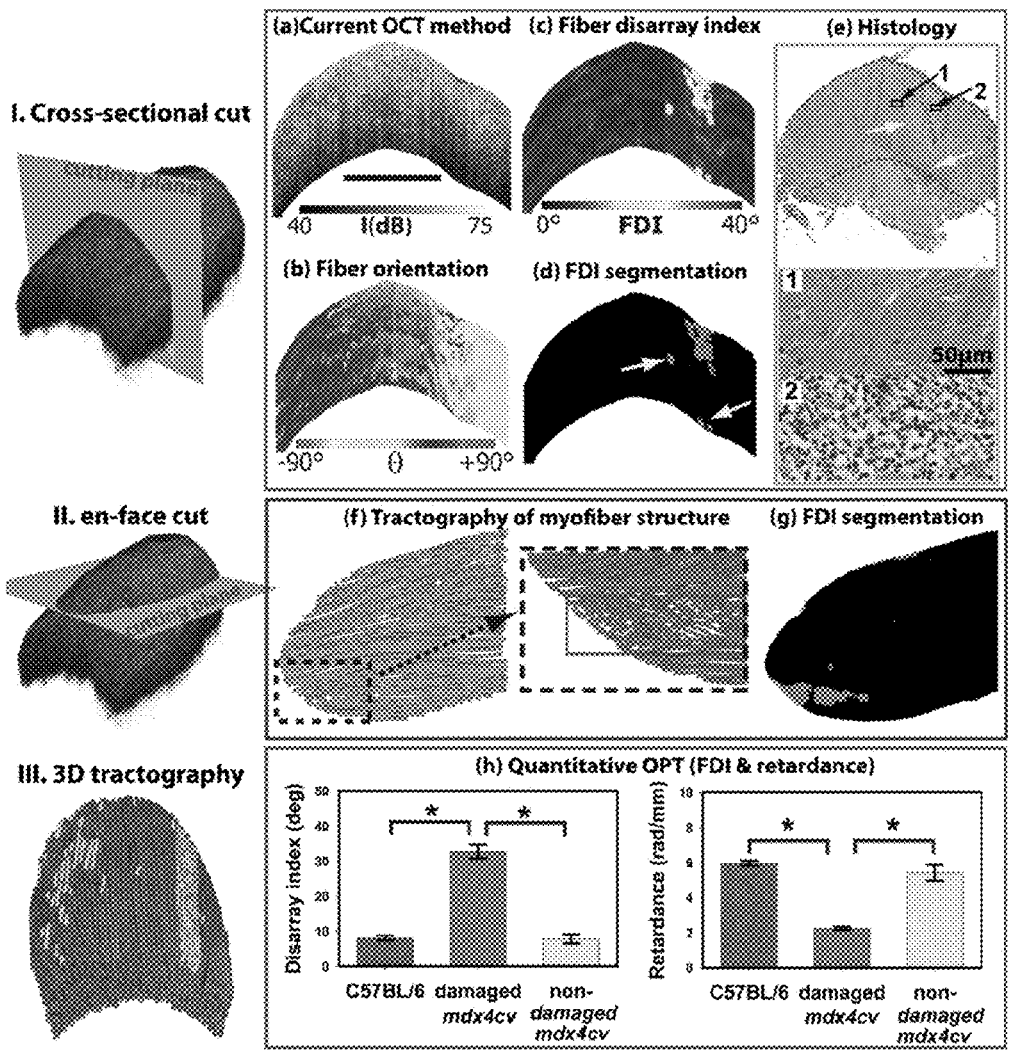
FIG. 12 provides images illustrative of use of the FDI system according to the invention using OPT imaging of an mdx4cv mouse TA muscle.

FIG. 12 shows example images obtained in a freshly excised whole tibialis anterior (TA) muscle from a 7-mo old mdx mouse. FIGS. 12a-e show co-registered OPT images and histology sectioning in the cross-sectional plane perpendicular to muscle fibers. The current OCT technology (FIG. 12a, showing a conventional intensity image) did not reveal any obvious abnormalities. However, the fiber orientation image (FIG.12b) showed abrupt fiber orientation changes in the upper-right location. This image feature was quantified using the "fiber disarray index" (FDI) which was constructed by calculating the variation of the local optic axis within a small 3D evaluation window (FIG. 12c). FIG. 12d shows the segmented results by assigning light gray color to all image pixels with a FDI higher than 16°. The FDI-based segmentation agreed extremely well with the histology results (FIG. 12e) where the small necrotic region located at the upper-right part of the muscle sample was marked with dashed lines. The lower inset of FIG. 12e shows the high resolution (40×) histology images of the two small region-of-interest (ROI) marked in the upper 2× histology image. ROI #1 represented a region of non-damaged muscle; whereas ROI #2 showed a region of significant muscle necrosis and inflammation.

Due to its destructive nature, conventional histology image can only be obtained in a specific cutting plane (FIG. 12a). However, the 3D OPT images can be processed in software so that detailed analyses can be performed in any evaluation planes. FIG. 12f shows an example evaluation in the en face plane that is perpendicular to the cutting plane in FIG. 12a. The fiber organization was easily visualized in the "tractographic" images (FIG. 12f). The muscle damage appears in the lower-left part of the fiber tractography. In regions with non-damaged muscle, the fiber bundles were long and well organized. However the fiber orientation was dramatically distorted in the damaged area (FIG. 12f). FIG. 12g shows that the damaged area (in light-gray color) can be segmented in this en face cutting plane based on FDI (e.g., FDI threshold of)16°.

The power of OPT is better illustrated in its ability to visualize the 3D tractography and to identify 3D lesions in the entire TA muscle (the bottom panel in FIG. 12). Such 3D segmentation allows a quantitative assessment of the overall muscle damage. FIG. 12h shows that the FDI was significantly higher (p<0.0001) in damaged mdx4cv muscles than in non-damaged mdx4cv muscles. In addition, damaged mdx4cv muscles also had a significantly smaller (p<0.0001) retardance value than non-damaged muscles.

While the invention has been shown and described with reference to certain exemplary embodiments thereof, it will be understood by those skilled in the related art that various changes in form and details may be made therein without departing from the scope of the invention as described otherwise herein and by the appended claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those skilled in the related art upon reviewing the above description. The scope of the various embodiments of the invention should, therefore, be determined with reference to the invention principles and appended claims, along with the full scope of equivalents to which such invention principles and claims are entitled.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention may include other examples that occur to those skilled in the art. Such other examples are intended to be within the scope of the invention and claims if the examples have structural elements that do not differ from the literal language of the claims, or if the examples include equivalent structural elements with insubstantial differences from the literal languages of the claims.

What is claimed is:

1. A method of producing 3D images of a fibrous target tissue sample, the method comprising:

focusing a polarized incident light with one or more optical polarizations in a first direction on one or more surface locations of a fibrous target tissue sample, whereby at each surface location of the incident light in the first direction the incident light propagates inside the fibrous target tissue sample and comes out from different depths within the fibrous target tissue sample to provide a first signal resulting from the incident light in the first direction;

analyzing polarization characteristics of the of first signal to derive fiber orientation data within the fibrous target tissue sample at each depth relative to a first projection plane defined by the first direction of the incident light and a 3D position of the fibrous target tissue sample;

constructing a first 3D image volume of fiber orientation of the fibrous target tissue sample utilizing the fiber orientation data derived at each depth relative to the first projection plane at each of the surface locations of the incident light in the first direction;

focusing the polarized incident light with one or more optical polarizations at at least one additional direction that is different than the first direction on one or more additional surface locations of the fibrous target tissue sample, whereby at each surface location of the incident light in the at least one additional direction the incident light propagates inside the fibrous target tissue sample and comes out from different depths within the fibrous target tissue sample to provide an additional signal resulting from the incident light in the at least one additional direction;

analyzing polarization characteristics of the additional signal to derive fiber orientation data at each depth within the fibrous target tissue sample relative to at least one additional projection plane defined by the at least one additional direction of the incident light and the 3D position of the fibrous target tissue sample;

constructing at least one additional 3D image volume of the fiber orientation of the fibrous target tissue sample utilizing the fiber orientation data derived at each of the depths relative to the at least one additional projection plane at each of the additional incident light surface locations;

registering the first 3D image volume of fiber orientation of the fibrous target tissue sample and the at least one additional 3D image volume of fiber orientation of the fibrous target tissue sample to construct a combined 3D image volume of 3D fiber orientation of the fibrous target tissue sample at the intersection of the first projection plane and the at least one additional projection plane;

determining 3D image properties of the fibrous target tissue sample utilizing the combined 3D image volume of the 3D fiber orientation of the fibrous target tissue sample; and transmitting the 3D image properties of the fibrous target tissue sample to a processor to produce 3D images of the fibrous target tissue sample.

2. The method of claim 1 wherein the fibrous target tissue sample is imaged in vivo.

3. The method of claim 1 wherein the fibrous target tissue sample is imaged using a surgical or dissecting microscope, or endoscopic device.

4. The method of claim 1 further comprising the step of displaying the fibrous target tissue sample's fiber orientation by distinctively displaying the fibrous target tissue sample's fiber orientation on a computer screen or directly on the fibrous target tissue sample.

5. The method of claim 1 wherein the first and the at least one additional 3D image volumes of fiber orientation of the fibrous target tissue sample are produced simultaneously.

6. The method of claim 1 wherein the first and the at least one additional 3D image volumes of fiber orientation of the fibrous target tissue sample are produced in sequence.

7. The method of claim 1 wherein the first and the at least one additional 3D volumes of fiber orientation of the fibrous target tissue sample are produced using the same light source.

8. The method of claim 1 wherein the first and the at least one additional 3D image volumes of fiber orientation of the fibrous target tissue sample are produced using a different light source.

* * * * *